(12) United States Patent
Abbott, Jr. et al.

(10) Patent No.: US 9,028,662 B2
(45) Date of Patent: May 12, 2015

(54) ELECTROCHEMICAL SENSING ARRAYS

(75) Inventors: James E. Abbott, Jr., Albany, OR (US);
Greg S. Long, Corvallis, OR (US);
Michael A. Delos-Reyes, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 240 days.

(21) Appl. No.: 13/545,149

(22) Filed: Jul. 10, 2012

(65) Prior Publication Data

US 2014/0014511 A1    Jan. 16, 2014

(51) Int. Cl.
*G01N 27/27* (2006.01)

(52) U.S. Cl.
CPC .......... *G01N 27/27* (2013.01); *Y10T 29/49204* (2015.01)

(58) Field of Classification Search
CPC ..... G01N 27/27; G01N 21/253; G01N 21/76; G01N 27/28; B01L 3/5085
USPC ............. 204/400, 403.01, 406, 409, 411, 412
See application file for complete search history.

(56) References Cited

U.S. PATENT DOCUMENTS

| | | | |
|---|---|---|---|
| 4,225,410 A * | 9/1980 | Pace | 204/412 |
| 7,341,834 B2 | 3/2008 | Yang | |
| 7,976,779 B2 | 7/2011 | Tai et al. | |
| 7,988,839 B2 | 8/2011 | Dorairaj et al. | |
| 2002/0090649 A1 * | 7/2002 | Chan et al. | 435/7.1 |
| 2011/0284395 A1 | 11/2011 | Dimitrakopoulos et al. | |

FOREIGN PATENT DOCUMENTS

WO    WO03081253    10/2003

OTHER PUBLICATIONS

Fragoso, et al., "Integrated Microfluidic Platform for the Electrochemical Detection of Breast Cancer Markers in Patient Serum Samples," Lab on a Chip Journal, vol. 11, Issue 4, Feb. 2011, pp. 625-631.
Edwards, et al., "A Parallel Microfluidic Channel Fixture Fabricated Using Laser Ablated Plastic Laminates for Electrochemical and Chemiluminescent Biodetection of DNA," Biomicrofluidics, vol. 5, Issue 4, Dec. 15, 2011, 14 pages.

* cited by examiner

*Primary Examiner* — J. Christopher Ball
*Assistant Examiner* — Maris R Kessel
(74) *Attorney, Agent, or Firm* — Brooks, Cameron & Huebsch, PLLC

(57) ABSTRACT

Methods, arrays, and systems for electrochemical sensing are provided. An example of a method includes forming a number of first electrodes, forming a fluidic level having a number of walls that extend substantially vertically from each of the number of first electrodes, and forming a number of second electrodes in contact with the number of walls. In some examples, forming the fluidic level having the number of walls includes embossing an embossing resin.

15 Claims, 5 Drawing Sheets

ELECTROCHEMICAL SENSING ARRAYS

BACKGROUND

Electrochemical analysis to identify particular chemical species in a sample may be conducted on individual samples each having a fixed concentration of the particular chemical species and/or a fixed volume, which may be in the millimeter range. The field of electrochemical analysis may be advanced by more efficient analyses utilizing, for instance, reduced sample size and/or reagent consumption, along with increased ability to input multiple samples and/or testing parameters.

DETAILED DESCRIPTION

Figure 1A:
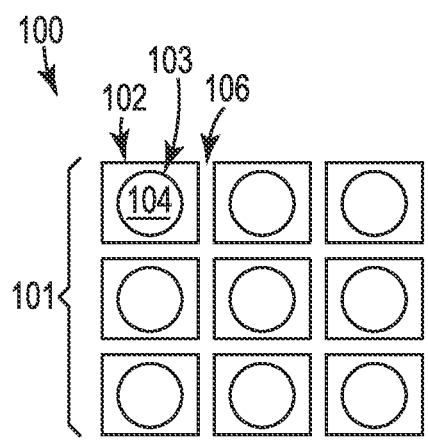
FIGS. 1A-1B illustrate an example of an electrochemical sensing array according to the present disclosure.

The present disclosure describes examples of formation and use of electrochemical sensing arrays having micro-scale electrochemical sensing cells (e.g., having height and/or breadth of 50 micrometers or less) that can be produced by high-volume manufacturing processes (e.g., in a roll-to-roll fabrication process, among others). Such micro-scale electrochemical sensing cells enable liquid sample sizes in the microliter to nanoliter volume range, which can reduce consumption of analytes (e.g., chemical species associated with a number of reagents, such as buffers). In addition, the electrochemical sensing arrays, as described herein, enable input of multiple analytes and/or application of variable testing parameters thereto.

As presented herein, in various examples, an array of electrodes can be formed (e.g., patterned upon an insulating substrate that may be rigid or flexible) upon which a fluidic layer is formed (e.g., by embossing, imprinting, electroforming, photoimaging, development of a photoimageable polymer, photomasking, gravure, deposition and etching, among other techniques). The fluidic layer can, in various examples, be utilized for introduction into and/or removal from the electrochemical sensing cells of liquid analytes carrying a number of (e.g., one or more) chemical species of interest. A number of electrodes (e.g., top electrodes) can be formed on (e.g., attached to) a surface of the fluidic layer opposite from the array of electrodes (e.g., bottom electrodes).

Operation of such electrochemical sensing arrays can, in various examples, be performed by directed control (e.g., via a processor executing instructions stored on a non-transitory computer-readable medium) of an electric field generated between the electrodes (e.g., the directed control being designed to detect particular chemical species). In some examples, the directed control of the electric field can include directed charging and/or discharging of the array of electrodes relative to the number of electrodes formed on the surface of the fluidic layer (e.g., in addition to electrodes possibly positioned at other locations, as described herein). Signals output from the electrochemical sensing cells of the array can be monitored and data can be collected (e.g., by a computing apparatus), thereby allowing for identification of particular chemical species.

In various examples, a plurality of electrochemical sensing cells can be separated by a number of walls in the fluidic level and introduction of a plurality of particular analytes (e.g., that vary in particular chemical species and/or concentration thereof present therein) can be controlled between the plurality of electrochemical sensing cells (e.g., via a processor that executes instructions to control introduction thereof). As such, different analytes can be directed to be introduced into different electrochemical sensing cells for separate and/or substantially simultaneous analysis thereof and/or the same analytes can be directed to be introduced into a plurality of electrochemical sensing cells for replicate analyses thereof based upon the directed control of the electric field generated between the electrodes.

Methods, arrays, and systems for electrochemical sensing are provided. An example of a method includes forming a number of first electrodes, forming a fluidic level having a number of walls that extend substantially vertically from each of the number of first electrodes, and forming a number of second electrodes in contact with the number of walls. In some examples, forming the fluidic level having the number of walls can include embossing an embossing resin, among other techniques presented herein.

Figure 1B:
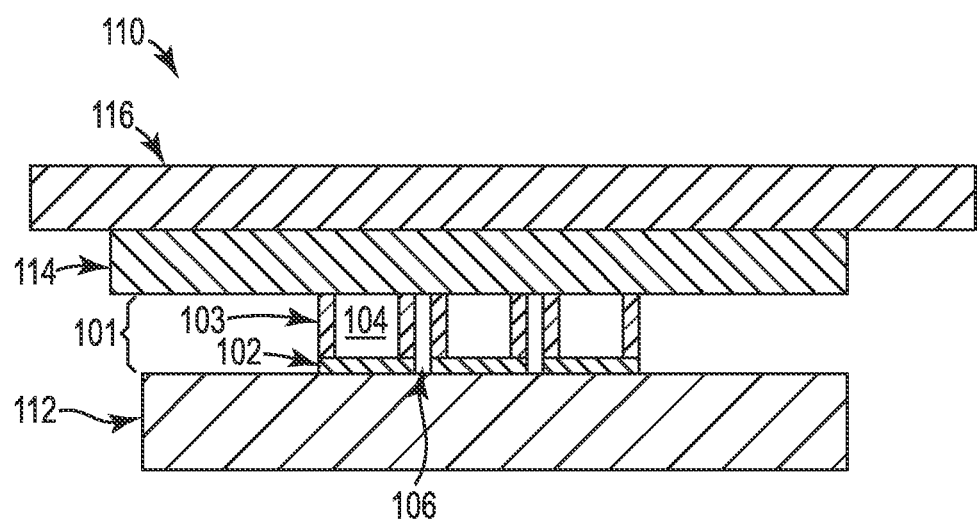

FIGS. 1A-1B illustrate an example of an electrochemical sensing array according to the present disclosure. A portion of an electrochemical sensing array 100 illustrated in FIG. 1A shows a cross-section viewed from a top of a fluidic level 101, as described herein. In various examples, the fluidic level 101 can include a number of electrodes 102. The number of electrodes 102 shown in the fluidic level 101 of FIG. 1A is nine (e.g., three rows of three electrodes) by way of example and not by way of limitation. That is, consistent with the present disclosure, the number of electrodes in the fluidic level can be one or more electrodes.

In various examples, each of the number of electrodes 102 can have a number of walls 103 formed thereon (e.g., via embossing an embossing resin, among other techniques presented herein). As described herein, a number of walls (e.g., wall 103) can extend substantially vertically from (e.g., above) each of a number of electrodes (e.g., electrode 102) to form a number of electrochemical sensing cells (e.g., electrochemical sensing cell 104) on each electrode. That is, each of the number of electrodes can have at least one electrochemical sensing cell with a number of walls that substantially enclose a perimeter of each electrochemical sensing cell to a particular height above the electrode (e.g., to form a well). The number of electrochemical sensing cells 104 shown in the fluidic level 101 of FIG. 1A is nine (e.g., three rows of three electrochemical sensing cells) by way of example and not by way of limitation. That is, consistent with the present disclosure, the number of electrochemical sensing cells in the fluidic level can be one or more electrochemical sensing cells.

In the detailed description of the present disclosure, reference is made to the accompanying drawings that form a part hereof and in which is shown by way of illustration how examples of the disclosure may be practiced. These examples are described in sufficient detail to enable one of ordinary skill in the art to practice the examples of this disclosure and it is to be understood that other examples may be utilized and that process, electrical, and/or structural changes may be made without departing from the scope of the present disclosure. Further, where appropriate, as used herein, "for example' and "by way of example" should be understood as abbreviations for "by way of example and not by way of limitation".

The figures herein follow a numbering convention in which the first digit or digits correspond to the drawing figure number and the remaining digits identify an element or component in the drawing. Similar elements or components between different figures may be identified by the use of similar digits. For example, 111 may reference element "11" in FIG. 1, and a similar element may be referenced as 211 in FIG. 2. Elements shown in the various figures herein may be added, exchanged, and/or eliminated so as to provide a number of additional examples of the present disclosure. In addition, the proportion and the relative scale of the elements provided in the figures are intended to illustrate the examples of the present disclosure and should not be taken in a limiting sense.

As illustrated in FIG. 1A, in various examples, the number of walls 103 can have a number of apertures (not shown) formed therein to enable introduction of an analyte into and/or removal of the analyte from the electrochemical sensing cell 104. To enable introduction of the analyte into and/or removal of the analyte from the electrochemical sensing cell 104, the fluidic layer 101 can include a number of fluidic channels 106. The number of fluidic channels 106 can, in various examples, be formed between the electrodes 102 and/or the walls 103 that form the electrochemical sensing cells 104 of the electrochemical sensing array 100.

As described herein, the electrochemical sensing cell (e.g., electrochemical sensing cell 104) formed on each electrode (e.g., electrode 102) is shown for ease of illustration and not by way of limitation to have a round wall (e.g., wall 103) formed within a perimeter of the electrode. However, in various examples, the wall or walls (e.g., depending upon the configuration of the electrochemical sensing cell) can be partially or completely formed within, co-extensive with, and/or overlapping the perimeter of the electrode.

FIG. 1A shows each electrochemical sensing cell 104 to be formed from a single wall 103 that, in combination with an electrode 102, forms a substantially round well by way of example and not by way of limitation. That is, consistent with the present disclosure, in various examples, one or more wall sections can be used to form one or more electrochemical sensing cells on each electrode, where a shape of each well can be independently selected from round, oval, square, triangular, rectangular, or other polygonal enclosures, among other shapes. In addition, in various examples, each electrochemical sensing cell can be independently selected to be wider at a bottom (e.g., adjacent the bottom electrode 102), a top, or a middle portion of the well dependent on particular configurations of the one or more walls thereof.

A portion of an electrochemical sensing array 110 illustrated in FIG. 1B shows a cross-section viewed from a side of a fluidic level 101, as described herein. As illustrated with regard to FIG. 1A, the fluidic level 101 can include a number of electrodes 102, in various examples. The number of electrodes 102 shown in the side view of the fluidic level 101 of FIG. 1B is three (e.g., three electrodes of one row of electrodes cut through a middle of the electrodes) by way of example and not by way of limitation. That is, consistent with the present disclosure, the number of electrodes in the fluidic level can be one or more electrodes.

The number of electrodes 102 can, in various examples, be formed on a substrate 112 (e.g., a bottom substrate). In various examples, a number of electrodes 114 (e.g., top electrodes) can be formed in contact with the walls 103 (e.g., in contact with an edge of the walls) distal from the bottom electrodes 102. Top, bottom, and/or electrodes positioned elsewhere (e.g., on a side of the electrochemical sensing cell 104) can be formed (e.g., patterned) into a number of electrodes (e.g., an array) using various techniques (e.g., via semiconductor deposition technology). Electrode 114 is shown to be one electrode by way of example and not by way of limitation. That is, in various examples, electrode 114 can be formed as a plurality of electrodes (e.g., up to one or more electrodes per electrochemical sensing cell 104).

In various examples, a substrate 116 can be formed on a side of the electrode or electrodes 114 opposite from the number of walls 103. As an alternative, the electrode or electrodes 114 can be formed on the substrate 116 and the pre-formed combination can be positioned on (e.g., adhered to) the number of walls 103. When substrate 112 and/or substrate 116 is included, either of the substrates can be formed as an insulating layer (e.g., formed from a non-conductive and/or a dielectric material) and/or either of the substrates 112, 116 can be formed to have an insulating layer between a substrate layer and adjacent electrodes to achieve electrical isolation. Substrates can include, for example, polymers of various types and/or glass-based materials, among others.

As described herein, the number of electrochemical sensing cells 104 (e.g., three in FIGS. 1A-1B and 2A-2B and four in FIGS. 3A-3B), and positioning thereof relative to the edges of the electrode 114 and/or the substrates 112, 116 is illustrated by way of example and not by way of limitation. That is, in various examples, the number of electrochemical sensing cells can be formed as a plurality of electrochemical sensing cells that are positioned in various configurations (e.g., for ease of fluidic access, among other considerations) relative to each other and/or the edges of the electrode 114 and/or the substrates 112, 116.

As described in the present disclosure, determining the behavior and/or identity of the particular chemical species in the number of analytes can be accomplished via electrochemical detection, which may include two, three, or more electrodes. Electrochemical detectors are generally known in the art, and a detailed description therefore will not be provided for sake of brevity. During electrochemical sensing of an analyte, electrodes participating in the sensing are in contact with fluid (e.g., the analyte itself and/or a buffer in which the analyte is suspended, dissolved, etc.) in order to provide adequate electrical contact. The various electrodes may be sized as desired and according to design parameters of the application. If currents and/or voltages to be applied are substantial, a suitable size can be selected to avoid the risk of bubble generation from electrolysis.

The electrodes may be referred to for convenience as work, reference, and auxiliary electrodes. For example, a constant voltage potential can be applied between a work electrode and a reference electrode, which may induce a constant base current flow through the two electrodes. When a particular chemical species in an analyte travels over the work electrode, a particular charge held by the particular chemical species may cause the particular chemical species to participate in an oxidation/reduction reaction with the work electrode. Electrons gained or lost by the work electrode, for example, may result in an increase or decrease in current, which may be indicative of (e.g., through signal processing) the presence of the particular chemical species in the analyte present in (e.g., flowing through) the electrochemical sensing cell, which in some examples can be used for quantification of the same. Accordingly, current and/or voltage responses across the electrodes, among other determinants of the electric field, can be measured, as described herein, to determine the behavior and/or identity of particular chemical species in a number of analytes (e.g., different analytes being introduced into different electrochemical sensing cells of the array).

Figure 2A:
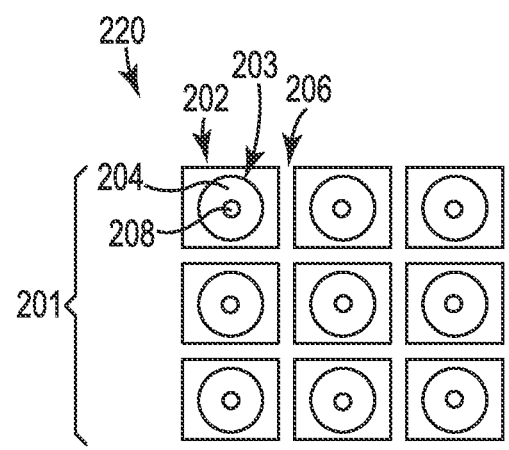
FIGS. 2A-2B illustrate another example of an electrochemical sensing array according to the present disclosure.
Figure 2B:
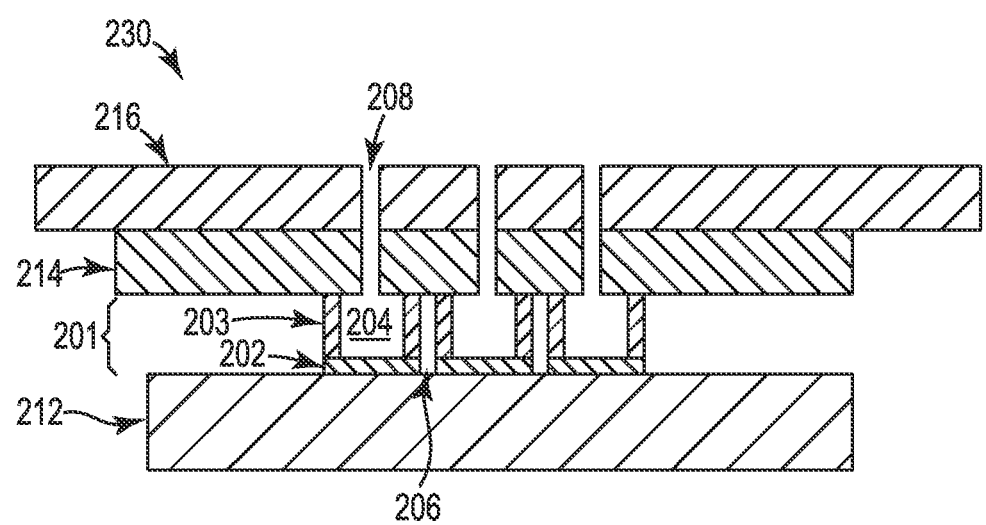

FIGS. 2A-2B illustrate another example of an electrochemical sensing array according to the present disclosure. Similar to FIG. 1A, a portion of an electrochemical sensing array 220 illustrated in FIG. 2A shows a cross-section viewed from a top of a fluidic level 201, as described herein. In various examples, the fluidic level 201 can include a number of electrodes 202. The number of electrodes 202 shown in the fluidic level 201 of FIG. 2A is nine (e.g., three rows of three electrodes) by way of example and not by way of limitation. That is, consistent with the present disclosure, the number of electrodes in the fluidic level can be one or more electrodes. The number of electrochemical sensing cells 204 shown in the fluidic level 201 of FIG. 2A is nine (e.g., three rows of three electrochemical sensing cells) by way of example and not by way of limitation. That is, consistent with the present disclosure, the number of electrochemical sensing cells in the fluidic level can be one or more electrochemical sensing cells.

In addition, or as an alternative, to the example illustrated in FIG. 1A, FIG. 2A illustrates that a number of apertures 208 can, in various examples, be formed through at least a top electrode 214 to enable introduction of an analyte into and/or removal of the analyte from the electrochemical sensing cell 204. To further enable introduction of the analyte into and/or removal of the analyte from the electrochemical sensing cell 204, the fluidic layer 201 can include a number of fluidic channels 206. The number of fluidic channels 206 can, in various examples, be formed between the electrodes 202 and/or the walls 203 that form the electrochemical sensing cells 204 of the electrochemical sensing array 220.

A portion of an electrochemical sensing array 230 illustrated in FIG. 2B shows a cross-section viewed from a side of a fluidic level 201, as described herein. As illustrated with regard to FIG. 2A, the fluidic level 201 can include a number of electrodes 202, in various examples. The number of electrodes 202 shown in the side view of the fluidic level 201 of FIG. 2B is three (e.g., three electrodes of one row of electrodes cut through a middle of the electrodes) by way of example and not by way of limitation. That is, consistent with the present disclosure, the number of electrodes in the fluidic level can be one or more electrodes.

The number of electrodes 202 can, in various examples, be formed on a substrate 212 (e.g., a bottom substrate). In various examples, a number of electrodes 214 (e.g., top electrodes) can be formed in contact with the walls 203 (e.g., in contact with an edge of the walls) distal from the bottom electrodes 202. Top, bottom, and/or electrodes positioned elsewhere (e.g., on a side of the electrochemical sensing cell 204) can be formed (e.g., patterned) into a number of electrodes (e.g., an array) using various techniques (e.g., via semiconductor deposition technology).

Electrode 214 is shown to be one electrode, with three apertures 208 therethrough at the position of the cross-section, by way of example and not by way of limitation. That is, in various examples, electrode 214 can be formed as a plurality of electrodes (e.g., up to one or more electrodes per electrochemical sensing cell 204) having an aperture in at least one of the electrodes.

In various examples, a substrate 216 can be formed on a side of the electrode or electrodes 214 opposite from the number of walls 203. When present, the substrate can, in various examples, have apertures 208 that intersect the apertures 208 in the electrode 214.

In various examples, an analyte can be introduced into a number of intended electrochemical sensing cells 204 through a number of apertures 208 that access each electrochemical sensing cell 204 (e.g., utilizing appropriate techniques, such as micro-pipette, syringe, ink-jet printing, among others). Adequate wetting of portions of the electrochemical sensing cells 204 can, for example, be confirmed via comparison of an initial impedance measurement across the electrodes.

Figure 3A:
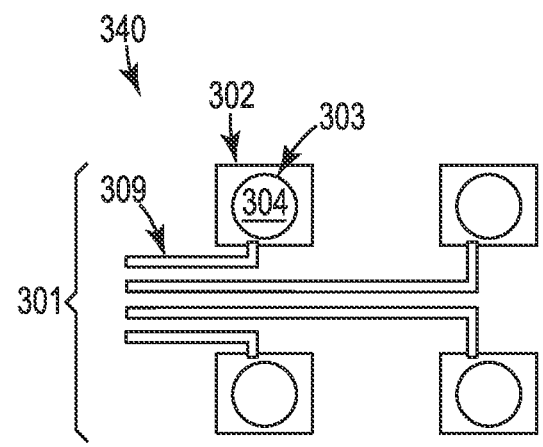
FIGS. 3A-3B illustrate other examples of an electrochemical sensing array according to the present disclosure.
Figure 3B:
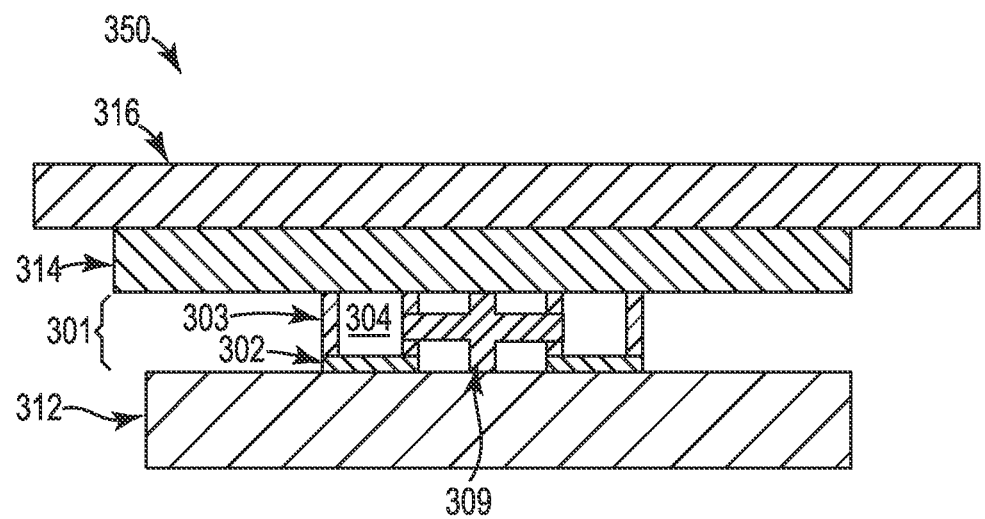

FIGS. 3A-3B illustrate other examples of an electrochemical sensing array according to the present disclosure. Similar to FIGS. 1A and 2A, a portion of an electrochemical sensing array 340 illustrated in FIG. 3A shows a cross-section viewed from a top of a fluidic level 301, as described herein. In various examples, the fluidic level 301 can include a number of electrodes 302. The number of electrodes 302 shown in the fluidic level 301 of FIG. 3A is four (e.g., two rows of two electrodes) by way of example and not by way of limitation. That is, consistent with the present disclosure, the number of electrodes in the fluidic level can be one or more electrodes.

The number of electrochemical sensing cells 304 shown in the fluidic level 301 of FIG. 3A is four (e.g., two rows of two electrochemical sensing cells) by way of example and not by way of limitation. That is, consistent with the present disclosure, the number of electrochemical sensing cells in the fluidic level can be one or more electrochemical sensing cells.

In addition, or as an alternative, to the examples illustrated in FIG. 1A and FIG. 2A, FIG. 3A illustrates that a number of fluidic channels 309 can, in various examples, be formed (e.g., via embossing an embossing resin, among other techniques presented herein) on, for example, substrate 312 to enable introduction of an analyte into and/or removal of the analyte from the electrochemical sensing cell 304. Each fluidic channel 309 can, in various examples, have a hollow configuration that enables direct introduction into and/or removal of the analyte from at least one electrochemical sensing cell 304.

A portion of an electrochemical sensing array 350 illustrated in FIG. 3B shows a cross-section viewed from a side of a fluidic level 301, as described herein. As illustrated with regard to FIG. 3A, the fluidic level 301 can include a number of electrodes 302, in various examples. The number of electrodes 302 shown in the side view of the fluidic level 301 of FIG. 3B is two (e.g., two electrodes of one row of electrodes cut through a middle of the electrodes) by way of example and not by way of limitation. That is, consistent with the present disclosure, the number of electrodes in the fluidic level can be one or more electrodes.

The number of fluidic channels 309 can, in various examples, be formed, for example, on the substrate 312 (e.g., a bottom substrate). In various examples, a number of electrodes 314 (e.g., top electrodes) can be formed in contact with the walls 303 (e.g., in contact with an edge of the walls) distal from the bottom electrodes 302. Top, bottom, and/or electrodes positioned elsewhere (e.g., on a side of the electrochemical sensing cell 304) can be formed (e.g., patterned) into a number of electrodes (e.g., an array) using various techniques (e.g., via semiconductor deposition technology). Electrode 314 is shown to be one electrode by way of example and not by way of limitation. That is, in various examples, electrode 314 can be formed as a plurality of electrodes (e.g., up to one or more electrodes per electrochemical sensing cell 304). In various examples, a substrate 316 can be formed on a side of the electrode or electrodes 314 opposite from the number of walls 303.

Each fluidic channel 309 can, in various examples, be formed to access at least one electrochemical sensing cell 304. The number of fluidic channels 309 that access each electrochemical sensing cell 304 shown in the side view of the fluidic level 301 of FIG. 3B is one by way of example and not by way of limitation. That is, consistent with the present disclosure, the number of fluidic channels 309 that access each electrochemical sensing cell 304 in the fluidic level can be one or more. The fluidic channel 309 illustrated in the cross-section of an alternative embodiment of FIG. 3B shows by way of example and not by way of limitation a vertical channel with a branch extending horizontally from each side thereof to penetrate a wall 303 of each of the two electrochemical sensing cells 304. That is, consistent with the present disclosure, fluidic channels can, in various examples, each have a single branch extending to a single electrochemical sensing cell (e.g., as shown in the embodiment of FIG. 3A), access a single electrochemical sensing cell without branching, and/or have a plurality of branches to access a plurality of electrochemical sensing cells, which can be positioned on either and/or both sides of the fluidic channel (e.g., as shown in the alternative embodiment of FIG. 3B).

In addition, a branch of the fluidic channel penetrating a wall of the electrochemical sensing cell is shown by way of example and not by way of limitation. That is, in various examples, the fluidic channel can access an electrochemical sensing cell by penetrating a side (e.g., wall 303), a bottom (e.g., electrode 302 and/or substrate 312), and/or a top (e.g., electrode 314) of the electrochemical sensing cell. Accordingly, in various examples, an analyte can be introduced into a number of intended electrochemical sensing cells 304 through number of fluidic channels 309 that access each electrochemical sensing cell 304.

In various examples, embossed structures (e.g., walls, as described herein) can be formed such that an electrode material originally below the embossing resin is exposed such that the electrode can be in contact with an analyte, and the chemical species within the analyte, present in an electrochemical sensing cell (e.g., a well) associated with the electrode. In various examples, an electrode (e.g., formed on a substrate) can be positioned (e.g., adhered) on top of the embossed structures. With at least two electrodes in contact with the analyte in the electrochemical sensing cell, electrochemical sensing (e.g., analysis) of the analyte can be performed.

Hence, electrochemical sensing arrays (e.g., consistent with the examples illustrated in FIGS. 1A-1B, 2A-2B, and 3A-3B) can include a plurality of first electrodes (e.g., bottom electrodes), a fluidic level having a number of walls that extend substantially vertically from (e.g., above) each of the plurality of first electrodes, and a number of second electrodes (e.g., top electrodes) in contact with ends of the number of walls that are distal from ends in contact with the plurality of first electrodes. A plurality of electrochemical sensing cells can, in various examples, be formed in the fluidic level. The number of walls can, in various examples, form a plurality of wells in combination with each of the plurality of first electrodes. A plurality of apertures can, as described herein in various examples, be formed through the number of second electrodes for introduction of a number of particular analytes into each of the plurality of wells (e.g., as illustrated in FIGS. 2A-2B).

A plurality of fluidic channels can, as described herein in various examples, be formed in the fluidic level for introduction of a number of particular analytes into each of the plurality of wells. For example, the fluidic channels can be positioned between the electrochemical sensing cells such that the walls of the electrochemical sensing cells substantially form walls for the fluidic channels (e.g., as illustrated in FIGS. 1A-1B and 2A-2B). Alternatively, or in addition, the fluidic channels can be formed (e.g., by embossing an embossing resin) having a hollow configuration that enables direct introduction into and/or removal of an analyte from at least one electrochemical sensing cell (e.g., as illustrated in FIG. 3A-3B). In various examples, at least one of the fluidic channels can be formed with electrochemical sensing functionality (e.g., with a number of electrodes positioned therein) to enable monitoring output signals thereof (e.g., to detect movement of particular chemical species therethrough).

Electrochemical analytic techniques (e.g., electrochemical impedance spectroscopy, among other techniques) can be sensitive to minute concentrations of chemical and/or biochemical species with an analyte. The structures and methods described herein are applicable to arrays of electrochemical cells formed in a microscopic scale (e.g., having height and/or breadth of 50 micrometers or less) or a macroscopic scale. The electrochemical cell array can be designed to couple a particular embossed configuration, for example, with a particular patterning of electrodes. In various examples, the electrodes can be formed as part of a passive array or the electrodes can be formed as part of an active matrix array (e.g., a thin firm transistor (TFT) array).

Figure 4:
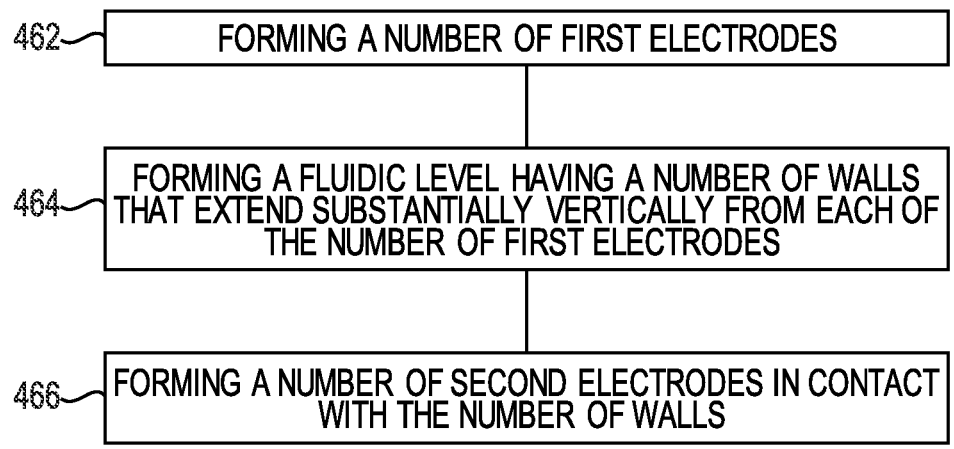
FIG. 4 is a block diagram illustrating an example of a method of forming an electrochemical sensing array according to the present disclosure.

FIG. 4 is a block diagram illustrating an example of a method of forming an electrochemical sensing array according to the present disclosure. Unless explicitly stated, the method examples described herein are not constrained to a particular order or sequence. Additionally, some of the described method examples, or elements thereof, can occur or be performed at the same, or substantially the same, point in time.

As described in the present disclosure, forming an electrochemical array, in various examples, includes forming a number of first electrodes, as shown in block 462. Forming the electrochemical array, in various examples, includes forming a fluidic level having a number of walls that extend substantially vertically from (e.g., above) each of the number of first electrodes, as shown in block 464. In addition, as shown in block 466, forming the electrochemical array, in various examples, includes forming a number of second electrodes in contact with the number of walls. By way of example and not by way of limitation, examples of various configurations for the first electrodes, the fluidic level, the walls, and the second electrodes, among other features, are presented with regard to FIGS. 1A-1B, 2A-2B, and 3A-3B. In various examples, the fluidic level having the number of walls can be formed by embossing an embossing resin, in addition or as an alternative to other techniques presented herein.

In various examples, forming the number of first electrodes can include forming a plurality of separate first electrodes on a substrate (e.g., the three separate electrodes being formed on a bottom substrate, as shown by way of example and not by way of limitation in FIGS. 1B, 2B, and 3B). Forming the plurality of separate first electrodes can include forming a plurality of electrochemical sensing cells separated by the number of walls in the fluidic level (e.g., the three separate electrochemical sensing cells being formed with substantially round walls, as shown by way of example and not by way of limitation in FIGS. 1A-1B, 2A-2B, and 3A-3B).

Forming the plurality of separate first electrodes can further include forming a number of fluidic channels in the fluidic level for introducing a number of analytes into the plurality of electrochemical sensing cells (e.g., the fluidic channels being formed as shown by way of example and not by way of limitation in FIGS. 1A-1B, 2A-2B, and 3A-3B). In various examples, forming the electrochemical array can include forming a substrate on a side of the number of second electrodes opposite from the number of walls (e.g., the top substrate being formed on the second electrode, as shown by way of example and not by way of limitation in FIGS. 1B, 2B, and 3B).

Advantages of the electrochemical sensing arrays described in the present disclosure include enablement of high-precision, high-output manufacture thereof. This, in turn, can enable new methods of chemical sensing, smaller configurations, lower chemical consumption for analysis, and/or lower cost for a given capability, among other potential advantages. Additional functionalities, for example, pumping and/or mixing of analytes, enabling of analyte to transit through and/or gas (e.g., air) to be removed from electrochemical sensing cells, among other functionalities, are enabled by the electrochemical sensing arrays described herein.

An example of an electrochemical sensing array system includes a number of processors to execute instructions that, for example, control an electric field generated between the electrodes to detect particular chemical species. That is, in various examples, the instructions and a resultant electric field are designed to detect particular chemical species in an analyte.

Figure 5:
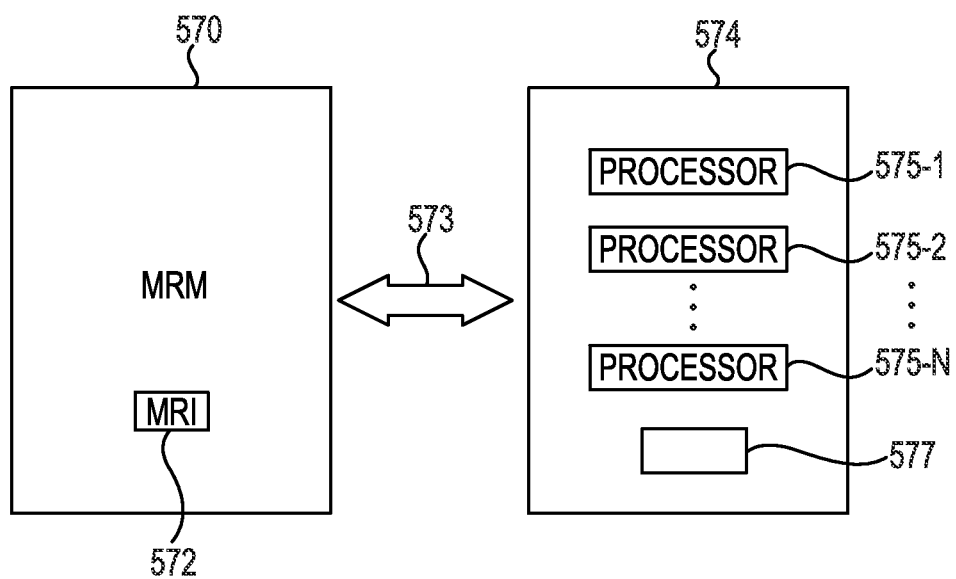
FIG. 5 is a block diagram illustrating an example of a machine readable medium with processing resources for electrochemical sensing arrays according to the present disclosure.

FIG. 5 is a block diagram illustrating an example of a machine readable medium (MRM) with processing resources for electrochemical sensing arrays according to the present disclosure. For example, the MRM 570 can be in communication via a communication path 573 with (e.g., operatively coupled to) a number of computing devices 574 having a number of processing resources 575-1, 575-2, . . . , 575-N (e.g., one or more processors). The MRM 570 can include machine readable instructions (MRI) 572 to cause the number of computing devices 574 to, for example, control an electric field generated between the electrodes to detect particular chemical species (e.g., by directed variance of the electric field), which can be executed in connection with particular applications.

For example, as described in the present disclosure, a non-transitory MRM 570 can have MRI 572 (e.g., computer executable instructions) stored thereon to direct a processor to execute instructions that control introduction of a plurality of particular analytes that vary between the plurality of electrochemical sensing cells separated by the number of walls in the fluidic level. That is, the MRI 572 can control introduction of different analytes into one or more particular electrochemical sensing cells, removal of the analytes therefrom, and/or replacement of the analyte in a particular electrochemical sensing cell with a different analyte or another sample of the same analyte, among other possibilities.

The MRI 572 of the MRM 570 can be executable by a processor to, for example, detect the particular chemical species in the plurality of particular analytes. That is, in various examples, the MRI 572 can be configured to control application of particular electric fields designed to detect particular chemical species in an analyte (e.g., in a particular buffered solution containing the chemical species). In various examples, the electric fields can be applied by a number of second electrodes that are in contact with ends of the number of walls that are distal from ends in contact with the plurality of first electrodes. In various examples, the system can include a number of third electrodes formed on a side of at least one of the number of walls.

The number of computing devices 574 can also include memory resources 577, and the processing resources 575-1, 575-2, . . . , 575-N can be coupled to these memory resources 577 in addition to those of the MRM 570. The MRM 570 can be in communication with the number of computing devices 574 having processing resources of more or fewer than 575-1, 575-2, . . . , 575-N. The number of computing devices 574 can be in communication with and/or receive from a tangible non-transitory MRM 570 storing a set of stored MRI 572 executable by one or more of the processing resources 575-1, 575-2, . . . , 575-N instructions for control of electrochemical sensing arrays, which can be executed in connection with particular applications. The stored MRI 572 can be an installed program or an installation pack. With an installation pack, the memory, for example, can be a memory managed by a server such that the installation pack can be downloaded.

The processing resources 575-1, 575-2, . . . , 575-N and the memory resource 577 can be local to a computing device, such as on a router, switch, server or other network device, etc. The machine readable medium 570 (e.g., a tangible, non-transitory computer readable medium) and/or the memory resource 577 can store a set of MRI 572 (e.g., program instructions in the form of software, firmware, etc.) executable by the processing resources 575-1, 575-2, . . . , 575-N.

Processing resources 575-1, 575-2, . . . , 575-N can execute the MRI 572 for, for example, control of electrochemical sensing arrays, which can be executed in connection with particular applications. A non-transitory MRM (e.g., MRM 570), as used herein, can include volatile and/or non-volatile memory. Volatile memory can include memory that depends upon power to store information, such as various types of random access memory (RAM), static random access memory (SRAM), dynamic random access memory (DRAM), among others. Non-volatile memory can include memory that does not depend upon power to store information. Examples of non-volatile memory can include solid state media such as flash memory, electronically erasable programmable read-only memory (EEPROM), phase change random access memory (PCRAM), magnetic memory such as a hard disk, tape drives, floppy disk, and/or tape memory, optical discs, digital video discs (DVD), Blu-ray discs (BD), compact discs (CD), and/or a solid state drive (SSD), etc., as well as other types of MRM.

The non-transitory MRM 570 can be integral, or communicatively coupled, to a computing device, in either in a wired or wireless manner. For example, the non-transitory MRM 570 can be an internal memory, a portable memory, a portable disk, or a memory located internal to another computing resource (e.g., enabling MRI M72 to be downloaded over the Internet).

The MRM 570 can be in communication with the processing resources 575-1, 575-2, . . . , 575-N via the communication path 573. The communication path 573 can be local or remote to a machine associated with the processing resources 575-1, 575-2, . . . , 575-N. Examples of a local communication path 573 can include an electronic bus internal to a machine such as a computing device where the MRM 570 is one of volatile, non-volatile, fixed, and/or removable storage medium in communication with the processing resources 575-1, 575-2, . . . , 575-N via the electronic bus. Examples of such electronic buses can include Industry Standard Architecture (ISA), Peripheral Component Interconnect (PCI), Advanced Technology Attachment (ATA), Small Computer System Interface (SCSI), Universal Serial Bus (USB), among other types of electronic buses and variants thereof.

The communication path 573 can be such that the MRM 570 is remote from the processing resources 575-1, 575-2, . . . , 575-N such as in the example of a network connection between the MRM 570 and the processing resources 575-1, 575-2, . . . , 575-N. That is, the communication path 573 can be a network connection. Examples of such a network connection can include a LAN, a WAN, a PAN, and the Internet, among others. In such examples, the MRM 570 may be associated with a first computing device and the processing resources 575-1, 575-2, . . . , 575-N may be associated with a second computing device.

It is to be understood that the above description has been made in an illustrative fashion, and not a restrictive one. Although specific examples for methods, devices, systems, computing devices, and instructions have been illustrated and described herein, other equivalent component arrangements, instructions, and/or device logic can be substituted for the specific examples shown herein. For example, "logic" is an alternative or additional processing resource to execute the actions, functions, etc., described herein, which includes hardware (e.g., various forms of transistor logic, application specific integrated circuits (ASICs), etc.), as opposed to machine executable instructions (e.g., software, firmware, etc.) stored in memory and executable by a processor.

What is claimed:

1. A method of forming an electrochemical sensing array, comprising:
   forming a plurality of electrochemical sensing cells, comprising;
      forming a number of first electrodes;
      forming a number of walls that extend substantially vertically from each of the number of first electrodes; and
      forming a number of second electrodes in contact with the number of walls;
   forming a fluidic level having the number of walls that extend substantially vertically from each of the number of first electrodes; and
   forming a number of fluidic channels in the fluidic level between an outside surface of the walls of at least two of the electrochemical sensing cells to introduce a number of analytes into at least one of the electrochemical sensing cells.

2. The method of claim 1, wherein forming the fluidic level having the number of walls comprises embossing an embossing resin.

3. The method of claim 1, further comprising forming a substrate on a side of the number of second electrodes opposite from the number of walls.

4. The method of claim 1, wherein forming the number of first electrodes comprises forming a plurality of separate first electrodes on a substrate.

5. The method of claim 4, wherein forming the plurality of separate first electrodes comprises forming the plurality of the electrochemical sensing cells separated by the number of walls in the fluidic level.

6. The method of claim 5, wherein forming the plurality of separate first electrodes comprises forming the number of fluidic channels in the fluidic level for introducing a number of analytes into the plurality of electrochemical sensing cells.

7. An electrochemical sensing array, comprising:
   a plurality of electrochemical sensing cells, comprising;
      a plurality of first electrodes; and
      a number of second electrodes in contact with ends of a number of walls that are distal from ends in contact with the plurality of first electrodes;
   a fluidic level having the number of walls that extend substantially vertically from each of the plurality of first electrodes; and
   a number of fluidic channels in the fluidic level formed between an outside surface of the walls of at least two of the electrochemical sensing cells formed to introduce a number of analytes into at least one of the electrochemical sensing cells.

8. The array of claim 7, comprising the plurality of the electrochemical sensing cells formed in the fluidic level.

9. The array of claim 7, wherein the number of walls form a plurality of wells in combination with each of the plurality of first electrodes.

10. The array of claim 9, comprising a plurality of apertures through the number of second electrodes for introduction of a number of particular analytes into each of the plurality of wells.

11. The array of claim 9, comprising a plurality of fluidic channels formed in the fluidic level for introduction of a number of particular analytes into each of the plurality of wells.

12. An electrochemical sensing array system, comprising:
   a plurality of electrochemical sensing cells, comprising;
      a plurality of first electrodes; and
      a number of second electrodes in contact with the number of walls;
   a fluidic level having the number of walls that extend substantially vertically from each of the plurality of first electrodes;
   a number of fluidic channels in the fluidic level formed between an outside surface of the walls of at least two of the electrochemical sensing cells formed to introduce a number of analytes into at least one of the electrochemical sensing cells; and
   a processor to execute instructions that control an electric field generated between the electrodes to detect particular chemical species.

13. The system of claim 12, wherein the number of second electrodes are in contact with ends of the number of walls that are distal from ends in contact with the plurality of first electrodes and wherein the system comprises a number of third electrodes formed on a side of at least one of the number of walls.

14. The system of claim 12, comprising the plurality of the electrochemical sensing cells separated by the number of walls in the fluidic level, wherein the processor executes instructions that control introduction of a plurality of particular analytes that vary between the plurality of electrochemical sensing cells.

15. The system of claim 14, comprising a non-transitory machine readable medium having processor-executable instructions stored thereon to detect the particular chemical species in the plurality of particular analytes.

* * * * *